(12) United States Patent
Okamoto et al.

(10) Patent No.: US 8,754,221 B2
(45) Date of Patent: *Jun. 17, 2014

(54) OPTICALLY ACTIVE CYCLIC ALCOHOL COMPOUND AND METHOD FOR PREPARING THE SAME

(71) Applicants: Masaki Okamoto, Osaka (JP); Akira Sakuragi, Osaka (JP); Yoshikazu Mori, Osaka (JP); Muneki Kishida, Osaka (JP); Takanori Higashijima, Osaka (JP)

(72) Inventors: Masaki Okamoto, Osaka (JP); Akira Sakuragi, Osaka (JP); Yoshikazu Mori, Osaka (JP); Muneki Kishida, Osaka (JP); Takanori Higashijima, Osaka (JP)

(73) Assignee: Mitsubishi Tanabe Pharma Corporation, Osaka-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/747,376

(22) Filed: Jan. 22, 2013

(65) Prior Publication Data

US 2013/0237708 A1    Sep. 12, 2013

Related U.S. Application Data

(60) Division of application No. 13/087,588, filed on Apr. 15, 2011, now Pat. No. 8,471,028, which is a continuation of application No. 12/089,170, filed as application No. PCT/JP2006/319846 on Oct. 4, 2006, now Pat. No. 7,989,627.

(30) Foreign Application Priority Data

Oct. 4, 2005   (JP) .................................. 2005-290756

(51) Int. Cl.
    *C07D 215/233*    (2006.01)
    *C07D 401/04*    (2006.01)

(52) U.S. Cl.
    USPC .................................................. 546/153

(58) Field of Classification Search
None
See application file for complete search history.

(56) References Cited

U.S. PATENT DOCUMENTS

| | | | |
|---|---|---|---|
| 5,969,140 A | 10/1999 | Ukita et al. | |
| 6,005,106 A | 12/1999 | Ukita et al. | |
| 7,972,836 B2 * | 7/2011 | Okamoto et al. | 435/280 |

FOREIGN PATENT DOCUMENTS

| | | |
|---|---|---|
| JP | H05-339263 A | 12/1993 |
| JP | 9-592555 | 3/1997 |
| JP | 10-226647 | 8/1998 |

OTHER PUBLICATIONS

Atwal, M. S. et al., "Analgetics. II. Relationship Between Structure and Activity of Some β-Amino Ketones," Journal of Medicinal Chemistry, vol. 12, No. 5, pp. 994-997 (1969).
Clemo, G. R. et al., "Synthesis of 4-Tetrahydroquinolone and a New Synthesis of 4-Methoxyquinoline," Journal of the Chemical Society, Transactions, vol. 125, pp. 1608-1622, (1924), with Chemical Abstracts, vol. 18, Abstract Nos. 24912, 3382i-3383a-i (1924).
Hashiguchi, S. et al., "Asymmetric Transfer Hydrogenation of Aromatic Ketones Catalyzed by Chiral Ruthenium(II) Complexes," J. Am. Chem. Soc., vol. 117, pp. 7562-7563, (1995).
Knapp, S. et al., "Synthesis and Kinetic Analysis of the N-Acetylhexosaminidase Inhibitor XyINAc-Isofagomine," J. Org. Chem., vol. 70, pp. 7715-7720, (2005).
Quallich, G. J. et al., "Enantioselective Oxazaborolidine Reduction of Ketones Containing Heteroatoms," Tetrahedron Letters, vol. 34, No. 5, pp. 785-788, (1993).
Silverman, The Organic Chemistry of Drug Design and Drug Action, Academic Press (1992).
Vippagunta et al., Crystalline Solids, 48 Adv. Drug Delivery Rev. 3-26 (2001).
Office Action mailed Sep. 17, 2010 in related U.S. Appl. No. 12/089,170, filed Apr. 3, 2008.
Amendment and Response to Restriction Requirement filed Oct. 7, 2010 in related U.S. Appl. No. 12/089,170, filed Apr. 3, 2008.
Office Action mailed Oct. 26, 2010 in related U.S. Appl. No. 12/089,170, filed Apr. 3, 2008.

(Continued)

*Primary Examiner* — Janet L Andres
*Assistant Examiner* — Timothy R Rozof
(74) *Attorney, Agent, or Firm* — Finnegan, Henderson, Farabow, Garrett & Dunner, L.L.P.

(57) ABSTRACT

The present invention relates to a method for preparing an optically active cyclic alcohol compound represented by general formula [I]:

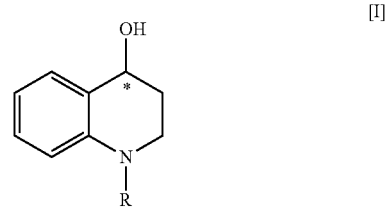

[wherein R represents a hydrogen atom or a protecting group for amino group, and * represents an asymmetric carbon atom.]
which comprises a step of subjecting a cyclic ketone compound represented by general formula [II]:

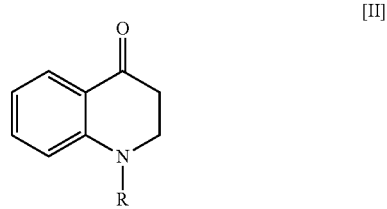

[wherein R has the same meaning as defined above.]
to asymmetric reduction (A) in the presence of an optically active oxazaborolidine compound and a boron hydride compound, or (B) in the presence of an asymmetric transition metal complex obtained from a transition metal compound and an asymmetric ligand and a hydrogen donor, and relates to said compound.

3 Claims, No Drawings

(56) References Cited

OTHER PUBLICATIONS

Amendment and Request for Reconsideration Under 37 C.F.R. 1.111 filed Feb. 2, 2011, including Declaration Under 37 C.F.R. 1.132 of Ryoko Ohno signed Jan. 25, 2011, in related U.S. Appl. No. 12/089,170, filed Apr. 3, 2008.
Notice of Allowance mailed Mar. 28, 2011 in related U.S. Appl. No. 12/089,170, filed Apr. 3, 2008.
Issue Notification dated Jul. 13, 2011 in related U.S. Appl. No. 12/089,170 filed Apr. 3, 2008.
Office Action mailed Jul. 12, 2011 in related U.S. Appl. No. 13/087,588, filed Apr. 15, 2011.
Request for Suspension of Action by Office filed Jan. 11, 2012 in related U.S. Appl. No. 13/087,588, filed Apr. 15, 2011.
Amendment and Request for Reconsideration Under 37, C.F.R. 1.111 (including attachments) filed Jan. 11, 2012 in related U.S. Appl. No. 13/087,588, filed Apr. 15, 2011.
Terminal Disclaimer filed Jan. 11, 2012 in related U.S. Appl. No. 13/087,588, filed Apr. 15, 2011.
Request for Termination of Suspension filed Feb. 8, 2012, including Declaration Under 37 C.F.R. 1.132 of Muneki Kishida signed Feb. 1, 2012, in related U.S. Appl. No. 13/087,588, filed Apr. 15, 2011.
Office Communication mailed Feb. 9, 2012, including Terminal Disclaimer Review Decision, in related U.S. Appl. No. 13/087,588, filed Apr. 15, 2011.
Notice of Allowance mailed Sep. 24, 2012 in related U.S. Appl. No. 13/087,588, filed Apr. 15, 2011.
Amendment After Notice of Allowance filed Dec. 13, 2012 in related U.S. Appl. No. 13/087,588, filed Apr. 15, 2011.
Submission Under 37 C.F.R. § 1.114 filed Dec. 20, 2012 in related U.S. Appl. No. 13/087,588, filed Apr. 15, 2011.
Request for Continued Examination filed Dec. 20, 2012 in related U.S. Appl. No. 13/087,588, filed Apr. 15, 2011.
English Translation of the Japanese Office Action for Patent Application No. 2011-166437; Notification of Reason for Rejection; dated Aug. 6, 2013.

* cited by examiner

OPTICALLY ACTIVE CYCLIC ALCOHOL COMPOUND AND METHOD FOR PREPARING THE SAME

RELATED APPLICATIONS

This application is a division of application Ser. No. 13/087,588, filed Apr. 15, 2011, now pending, which is a continuation of application Ser. No. 12/089,170, filed Apr. 3, 2008, issued as U.S. Pat. No. 7,989,627 on Aug. 2, 2011, which is a National Stage of International Application No. PCT/JP2006/319846, filed Oct. 4, 2006, which claims priority to Japanese Application No. 2005-290756, filed Oct. 4, 2005, all of which are incorporated herein by reference.

TECHNICAL FIELD

The present invention relates to an optically active cyclic alcohol compound (an optically active 4-hydroxytetrahydroquinoline compound) useful as a synthetic intermediate for pharmaceutical compounds, and a method for preparing the same. Furthermore, the present invention relates to a method for preparing an optically active naphthalene compound, comprising utilizing the optically active alcohol compound.

BACKGROUND ART

Generally, from the view point of intended pharmacological activities, side-effects and the like, pharmaceutical compounds having an asymmetric center in the molecule are desirable to be used in their optically active form instead of in racemic form. A racemic naphthalene compound (Patent literature 1) represented by general formula [A-2]:

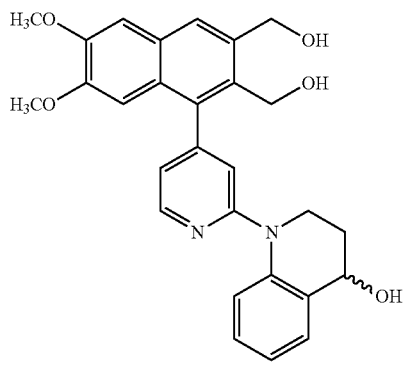

[A-2]

which is known to possess cAMP-specific phosphodiesterase (PDE4) inhibitory activity and be useful as anti-asthma drugs and the like, has one asymmetric carbon atom in the molecule, and therefore it is considered that the compound is desirable to be applied to clinical use in the optically active form. It is known that the compound [A-2] can be obtained by reacting a compound represented by formula [B-1]:

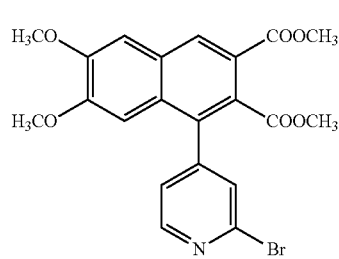

[B-1]

with 4(1H)-quinolinone compound represented by formula [B-2]:

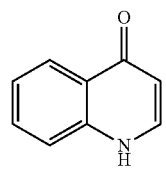

[B-2]

and then reducing the reaction product with sodium borohydride (Patent literature 1). However, the corresponding optically active form per se or a method for preparing the same (optical resolution methods of racemic form, asymmetric synthesis methods and the like) has not been reported so far.

From the viewpoint of synthetic chemistry, upon preparing an optically active form of the compound [A-2], there is considered a method of using an optically active cyclic alcohol compound (an optically active tetrahydroquinoline compound) represented by general formula [Ib]:

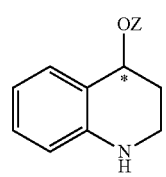

[Ib]

[wherein Z represents a protecting group for hydroxyl group, and * represents an asymmetric carbon atom.] as a synthetic intermediate, instead of using the compound [B-2]. However, the optically active cyclic alcohol compound per se is a novel compound, and of course a method for preparing the same has not been reported so far. Under the circumstances, in order to establish a method for preparing an optically active form of the compound [A-2] comprising using the above-mentioned optically active cyclic alcohol compound, it is required to develop a method for preparing the optically active cyclic alcohol compound with high optical purity and good yield.

Generally, as a method for preparing optically active alcohol compounds, for example, the following methods may be assumed: (1) a method comprising subjecting the corresponding prochiral ketone compound to asymmetric reduction in the presence of optically active oxazaborolidine compounds (CBS catalyst) (Nonpatent literatures 1 and 2); (2) a method comprising subjecting the corresponding prochiral ketone compound to asymmetric reduction in the presence of an asymmetric transition metal complex obtained from a transition metal compound and an asymmetric ligand (Nonpatent literature 3); or (3) a method comprising subjecting the corresponding prochiral ketone compound to asymmetric acylation with lipase (Nonpatent literature 4), etc. However, with regard to cyclic ketone compounds containing a carbonyl carbon and a hetero atom (nitrogen atom) in the same ring moiety such as tetrahydroquinolinone, consideration of possible application of asymmetric reduction or asymmetric acylation methods as mentioned above has not been reported so far.

The present inventors have been earnestly studied and as a result, they have found that an optically active alcohol compound [I] can be prepared with high optical purity and good yield from the corresponding cyclic ketone compound [II] by using an asymmetric reduction catalyst such as CBS catalyst, and completed the present invention.

[Patent literature 1] European Patent No. 748805 (see page 2)

[Nonpatent literature 1] E. J. Corey et al., Journal of The American Chemical Society, Vol. 109, pp. 7925-7926 (1987) (see page 7925)

[Nonpatent literature 2] G. J. Quallich et al., Tetrahedron Letters, Vol. 34, No. 5, pp. 785-788 (1993) (see page 785)

[Nonpatent literature 3] S. Hshiguchi et al., Journal of the American Chemical Society, Vol. 117, pp. 7562-7563 (1995) (see page 7562) [Nonpatent literature 4] J. Uenishi et al., Journal of Organic Chemistry Vol. 63, pp. 2481-2487 (1998) (see page 2482, lines 18 to 25 at left column)

DISCLOSURE OF THE INVENTION

Problems to be Solved by the Invention

The present invention provides a method for preparing an optically active cyclic alcohol compound (an optically active 1,2,3,4-tetrahydro-4-quinolinol compound) useful as a synthetic intermediate for pharmaceutical compounds such as optically active naphthalene compounds, with industrial advantage, and said compound per se. Also, the present invention provides a method for preparing an optically active naphthalene compound comprising using said optically active synthetic intermediate, and said optically active naphthalene compound per se.

Means to Solve the Problems

The present invention relates to a method for preparing an optically active cyclic alcohol compound represented by general formula [I]:

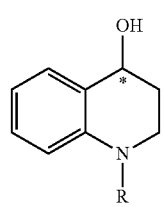

[I]

[wherein R represents a hydrogen atom or a protecting group for amino group, and * represents an asymmetric carbon atom.]

which comprises a step of subjecting a cyclic ketone compound represented by general formula [II]:

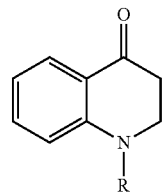

[II]

[wherein R has the same meaning as defined above.]

to asymmetric reduction (A) in the presence of an optically active oxazaborolidine compound (CBS catalyst) and a boron hydride compound, or (B) in the presence of an asymmetric transition metal complex obtained from a transition metal compound and an asymmetric ligand, and a hydrogen donor.

The present invention also relates to an optically active cyclic alcohol compound represented by general formula [S-I]:

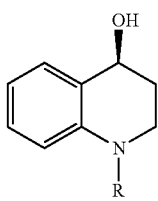

[S-I]

[wherein R represents a hydrogen atom or a protecting group for amino group.]

or general formula [R-I]:

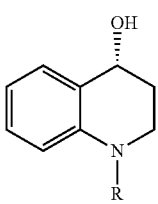

[R-I]

or salts thereof.

Also, the present invention relates to a method for preparing an optically active naphthalene compound represented by general formula [A]:

[chemical structure [A]]

[wherein the symbols have the same meaning as defined above.]

which comprises the steps of utilizing the optically active cyclic alcohol compound [I].

One aspect of the present invention is a method for preparing an optically active naphthalene compound represented by general formula [A]:

[chemical structure [A]]

which comprises the following steps of (a) to (c):

(a) reacting a compound represented by general formula [Ib]:

[chemical structure [Ib]]

[wherein Z represents a protecting group for hydroxyl group, and * represents an asymmetric carbon atom.] with a compound represented by general formula [III]:

[chemical structure [III]]

[wherein Ra and Rb are the same or different and each represents a hydrogen atom or a protecting group for carboxyl group, and X represents a halogen atom.] to obtain an optically active naphthalene compound represented by general formula [IV]:

[chemical structure [IV]]

[wherein the symbols have the same meaning as defined above.];

(b) reducing the compound [IV] to obtain an optically active 2,3-bishydroxymethylnaphthalene compound represented by general formula [V]:

[chemical structure [V]]

[wherein the symbols have the same meaning as defined above.]; and (c) removing the protecting group Z for hydroxyl group from the compound [V].

Further, the present invention relates to an optically active naphthalene compound represented by general formula [A]:

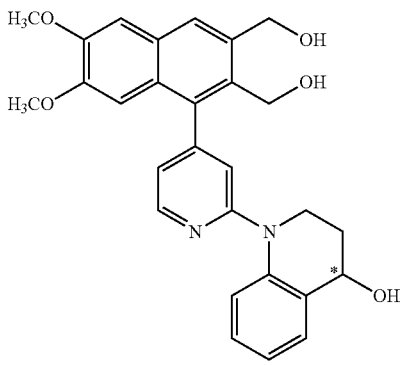

[A]

[wherein * represents an asymmetric carbon atom.], and hydrates thereof or pharmaceutically acceptable salts thereof.

One embodiment of the present invention is 1-[2-[(4S)-4-hydroxy-1,2,3,4-tetrahydroquinolin-1-yl]-4-pyridyl]-2,3-bis(hydroxymethyl)-6,7-dimethoxynaphthalene, and hydrates thereof or pharmaceutically acceptable salts thereof.

Other embodiment of the present invention is 1-[2-[(4R)-4-hydroxy-1,2,3,4-tetrahydroquinolin-1-yl]-4-pyridyl]-2,3-bis(hydroxymethyl)-6,7-dimethoxynaphthalene, and hydrates thereof or pharmaceutically acceptable salts thereof.

Effects of the Invention

According to the present invention, an optically active cyclic alcohol compound (an optically active 4-hydroxytetrahydroquinoline compound) useful as a synthetic intermediate for pharmaceutical compounds such as the optically active naphthalene compound [A] having excellent PDE4 inhibiting property, can be produced with industrial advantage.

BEST MODE TO CARRY OUT THE INVENTION

In the cyclic ketone compound [II] which is a raw material compound (substrate compound) of the present invention, when R is a protecting group for amino group, the protecting group may include an aryl-lower alkylcarbonyl group such as a benzyloxycarbonyl group, a lower alkoxycarbonyl group such as an ethoxycarbonyl group or a tert-butoxycarbonyl group, or a lower alkanoyl group optionally substituted by a halogen(s) such as an acetyl group or a trifluoroacetyl group. Among them, a benzyloxycarbonyl group is preferred.

(Method A)

Asymmetric Reduction of Cyclic Ketone with Oxazaborolidine Compound

An oxazaborolidine compound(s) to be used in the present invention means 1,3,2-oxazaborolidine derivatives (hereinafter also referred to as CBS catalyst) having a property of catalyzing stereoselective hydrogen transfer (hydride transfer) from boron hydride compounds to a carbonyl carbon of a substrate (ketone compound). Such an oxazaborolidine compound may include, for example, a compound represented by following general formula [a]:

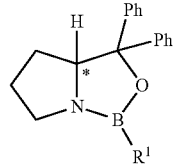

[a]

[wherein $R^1$ represents a lower alkyl group or a phenyl group, Ph represents a phenyl group, and * represents an asymmetric carbon atom.]

(Tetrahedron Letters, Vol. 34, No. 5, pp. 785-788 (1993)), and the like. A preferred compound of general formula [a] may include, for example, a compound represented by general formula [R-a]:

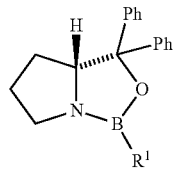

[R-a]

[wherein the symbols have the same meaning as defined above.], and a compound represented by general formula [S-a]:

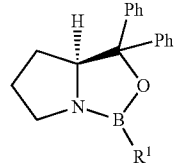

[S-a]

[wherein the symbols have the same meaning as defined above.].

A specific example of the above-mentioned compound [a] may include compounds wherein $R^1$ is methyl group, butyl group, phenyl group or the like, etc. Among them, preferred is (R)-2-methyl-CBS-oxazaborolidine or (S)-2-methyl-CBS-oxazaborolidine as represented by the following formulae:

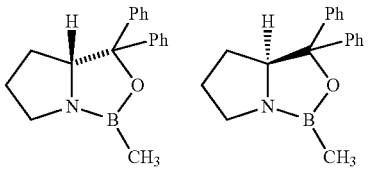

According to the present invention, both of the optically active alcohol compounds can be easily obtained by using CBS catalyst (oxazaborolidine compound) properly depending on the intended compound. For example, the optically active (4S)-alcohol compound [I] can be obtained by hydrogenaration of the compound [II] with (R)-oxazaborolidine compound [R-a], while the optically active (4R)-alcohol compound [I] can be obtained by hydrogenaration of the compound [II] with (S)-oxazaborolidine compound [S-a].

Boron hydride compounds may include, for example, diborane, borane-tetrahydrofuran complex, borane-dimethylsulfide complex, borane-1,4-oxathiane complex, borane-dimethylaniline complex, borane-diethylaniline complex, borane-4-phenylmorpholine complex, catecholborane or the like. Among them, preferred is borane-tetrahydrofuran complex or borane-dimethylsulfide complex.

The asymmetric reduction reaction of the cyclic ketone compound [II] using CBS catalyst and boron hydride compounds can be conducted in the presence or absence of a suitable solvent.

Upon conducting the present reaction, an oxazaborolidine compound (for example, the compound [a]), a boron hydride compound and the cyclic ketone compound [II] may be added to the reaction system simultaneously, or a complex of the oxazaborolidine compound and the boron hydride compound may be prepared in advance and then the cyclic ketone compound [II] may be added thereto.

As a solvent, any solvent may be used so long as it has no influence on asymmetric reduction reaction. Such a solvent may include tetrahydrofuran, dichloromethane, chloroform, toluene, cyclopentylmethyl ether, 1,2-dimethoxy ethane and the like.

An amount of CBS catalyst is 0.001 to 3 equivalent(s) to the amount of the cyclic ketone compound [II], preferably 0.01 to 0.3 equivalent. An amount of boron hydride compound to be used is 0.1 to 10 equivalent(s) to the amount of the cyclic ketone compound [II], preferably 0.5 to 3 equivalent(s).

The present asymmetric reduction reaction can be conducted at −20 to 60° C., preferably at 0 to 40° C.

The present asymmetric reduction-reaction time, which may differ depending on the reaction condition, is 1 to 24 hour(s), preferably 2 to 3 hours.

(Method B)
Asymmetric Reduction of Cyclic Ketone with Asymmetric Transition Metal Complex As an asymmetric transition metal complex to be used in the present invention, there may be used, for example, a complex which is obtained from a transition metal compound and an asymmetric ligand and possesses a property of catalyzing hydrogen transfer asymmetric reduction (asymmetric transfer hydrogenation) of the cyclic ketone compound [II] in the presence of a hydrogen donor.

A transition metal compound for preparing the asymmetric transition metal complex may include, for example, a transition metal-arene complex, transition metal-olefin complex, transition metal-carbonyl complex and the like. A metal species in said compound may include, for example, ruthenium, rhodium, iridium, cobalt and the like. Among them, ruthenium is preferred. Specific examples of the transition metal compound may include, for example, ruthenium-arene complex such as tetrachlorobis(benzene)diruthenium ([RuCl$_2$(C$_6$H$_6$)]$_2$), tetrachlorobis(p-cymene)diruthenium ([RuCl$_2$(C$_{10}$H$_{14}$)]$_2$), tetrachlorobis(hexamethylbenzene)diruthenium ([RuCl$_2$(C$_{12}$H$_{18}$)]$_2$), tetrachlorobis(mesitylene)diruthenium ([RuCl$_2$(C$_9$H$_{12}$)]$_2$), tetrachlorobis(ethyl benzoate)diruthenium ([RuCl$_2$(C$_9$H$_{10}$O$_2$)]$_2$), tetrabromobis(benzene)diruthenium ([RuBr$_2$(C$_6$H$_6$)]$_2$), tetrabromobis(p-cymene)diruthenium ([RuBr$_2$(C$_{10}$H$_{14}$)]$_2$), tetrabromobis(mesitylene)diruthenium ([RuBr$_2$(C$_9$H$_{12}$)]$_2$), tetraiodobis(benzene)diruthenium ([RuI$_2$(C$_6$H$_6$)]$_2$), tetraiodobis(p-cymene)diruthenium ([RuI$_2$(C$_{10}$H$_{14}$)]$_2$) or tetraiodobis(mesitylene)diruthenium ([RuI$_2$(C$_9$H$_{12}$)]$_2$), etc.

A asymmetric ligand for preparing the asymmetric transition metal complex may include, for example, an optically active alkylenediamine compound represented by the following general formula [b]:

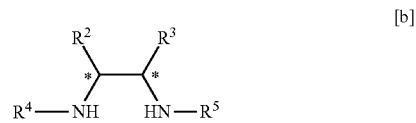

[b]

[wherein R$^2$ and R$^3$ each independently represent an optionally substituted lower alkyl group, an optionally substituted aryl group or an optionally substituted aromatic heterocyclic group, or R$^2$ and R$^3$ are taken together to form a cyclic group, R$^4$ and R$^5$ each independently represent a hydrogen atom, a lower alkyl group, an acyl group, an optionally substituted carbamoyl group, a thioacyl group, an optionally substituted thiocarbamoyl group, an optionally substituted lower alkylsulfonyl group or an optionally substituted arylsulfonyl group, and * represents an asymmetric carbon atom.]

and the like.

In the general formula [b], R$^2$ and R$^3$ represent an optionally substituted lower alkyl group such as methyl group, chloromethyl group, ethyl group, n-propyl group or isopropyl group; an optionally substituted aryl group such as phenyl group, naphthyl group, 4-methylphenyl group, 3,5-dimethylphenyl group or 4-methoxyphenyl group; an optionally substituted aromatic heterocyclic group such as furyl group or pyridyl group; or R$^2$ and R$^3$ are taken together to form a cyclic group such as tetraethylene group (these groups may be optionally substituted by one or more group(s) selected from a lower alkoxy group (methoxy group, ethoxy group or the like) and a halogen atom (a chlorine atom, a bromine atom, a fluorine atom or the like)), R$^4$ and R$^5$ independently represent a hydrogen atom; a lower alkyl group such as methyl group, ethyl group, n-propyl group or isopropyl group; an acyl group such as an acetyl group, propionyl group or benzoyl group; an optionally substituted carbamoyl group such as carbamoyl group, methylcarbamoyl group or phenylcarbamoyl group; a thioacyl group such as thioacetyl group, thiopropionyl group or thiobenzoyl group; an optionally substituted thiocarbamoyl group such as thiocarbamoyl group, methylthiocarbamoyl group or phenylthiocarbamoyl group; an optionally substituted lower alkylsulfonyl group such as methanesulfonyl group, trifluoromethanesulfonyl group or ethanesulfonyl group; an optionally substituted arylsulfonyl group such as benzenesulfonyl group, toluenesulfonyl group, 2,4,6-mesitylsulfonyl group, 2,4,6-triisopropylbenzenesulfonyl group, 4-methoxybenzenesulfonyl group, 4-chlorobenzenesulfonyl group or 2-naphthylsulfonyl group.

Among the above-mentioned asymmetric ligand (the compound [b]), preferred is a compound wherein one of R$^4$ and R$^5$ is a hydrogen atom or a lower alkyl group, and the other is an optionally substituted arylsulfonyl group.

As a more preferred compound [b], there may be mentioned, for example, an optically active alkylenediamine compound represented by the following general formula [b1]:

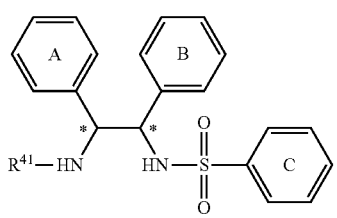

[wherein Ring A, Ring B and Ring C each independently represent a benzene ring optionally substituted by 1 to 5 group(s) selected from a lower alkyl group, a halogen atom and a lower alkoxy group, $R^{41}$ represents a hydrogen atom or a lower alkyl group, and * represents an asymmetric carbon atom.].

Specific examples of the above-mentioned optically active diamine compounds may include, for example, (S,S)— or (R,R)—N-tosyl-1,2-diphenylethylenediamine; (S,S)— or (R,R)—N-methyl-N'-tosyl-1,2-diphenylethylenediamine; (S,S)— or (R,R)—N-p-methoxyphenylsulfonyl-1,2-diphenylethylenediamine; (S,S)— or (R,R)—N-p-chlorophenylsulfonyl-1,2-diphenylethylenediamine; (S,S)— or (R,R)—N-p-mesitylsulfonyl-1,2-diphenylethylenediamine; or (S,S)— or (R,R)—N-(2,4,6-tri-isopropylphenyl)sulfonyl-1,2-diphenylethylenediamine, etc.

Among the above-mentioned asymmetric ligands, (S,S)— or (R,R)—N-tosyl-1,2-diphenylethylenediamine [(S,S)— or (R,R)-TsDPEN] are preferred.

According to the present invention, both of the optically active alcohol compounds can be easily obtained by using the asymmetric ligand properly depending on the intended compound. For example, the optically active (4S)-alcohol compound [I] can be obtained by using (S,S)—N-tosyl-1,2-diphenylethylenediamine, while the optically active (4R)-alcohol compound [I] can be obtained by using (R,R)—N-tosyl-1,2-diphenylethylenediamine.

The above-mentioned asymmetric transition metal complex can be prepared according to known methods, for example, a method described in Journal of the American Chemical Society, Vol. 117, pp. 7562-7563 (1995), etc. On this occasion, for example, by using a ruthenium-arene complex compound and the optically active diamine compound [b1], an asymmetric transition metal complex represented by the following general formula [C]:

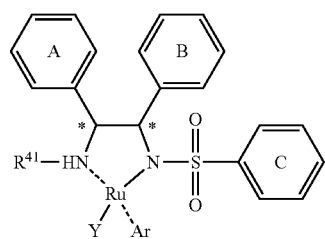

[wherein Y represents a halogen atom, Ar represents an optionally substituted aryl group, and the other symbols have the same meaning as defined above.]
can be obtained.

In the general formula [C], a halogen atom represented by Y may include a chlorine atom, an iodine atom, a bromine atom and the like. Also, when Ar is a substituted aryl group, said aryl group may include, for example, a phenyl group substituted by 1 to 6 lower alkyl group(s), etc.

Asymmetric reduction reaction of the cyclic ketone compound [II] with the asymmetric transition metal complex obtained as mentioned above can be conducted in the presence of a hydrogen donor, in the presence or absence of base, and in the presence or absence of a suitable solvent.

Upon conducting the present asymmetric reduction reaction, it is preferred that, as mentioned above, an asymmetric transition metal complex is prepared in advance and then the cyclic ketone compound [II] is added thereto. However, a transition metal compound, an asymmetric ligand and the cyclic ketone compound [II] may be added into a reaction system simultaneously.

A hydrogen donor may include, for example, a lower alkanol having a hydrogen atom(s) at α position (methanol, ethanol, n-propanol, isopropanol, n-buthanol, sec-buthanol and the like) or formic acid compounds (formic acid, formic acid ester, ammonium formate and the like). Among them, an isopropanol is preferred.

A base may include, for example, alkali metal hydroxide such as lithium hydroxide, sodium hydroxide or potassium hydroxide, alkali metal alkoxide such as lithium methoxide, sodium methoxide or potassium isopropoxide, and organic amines such as trimethylamine or triethylamine.

In the asymmetric reduction reaction of the present invention, the above-mentioned hydrogen donor (a lower alkanol, etc.) serves also as a solvent, so that it is not particularly necessary to use other solvents. However, if a solvent is used, the solvent may include, for example, dichloromethane, chloroform, toluene, chlorobenzene, tetrahydrofuran and the like.

An amount of the asymmetric transition metal complex in the present asymmetric reduction reaction is 0.005 to 1 equivalent to the amount of the cyclic ketone compound [II], preferably 0.01 to 0.1 equivalent. An amount of the hydrogen donor to be used is 1 to 1000 equivalent(s) to the amount of the cyclic ketone compound [II], preferably 5 to 300 equivalents. An amount of base to be used is 0.1 to 5 equivalent(s) to the compound [II], preferably 0.3 to 1 equivalent.

The present reaction can be carried out at −20 to 80° C., preferably at 0 to 50° C.

The present asymmetric reduction reaction time, which may differ depending on the reaction condition, is 3 to 24 hours, preferably 15 to 20 hours.

Separation/purification of the objective substance (an optically active cyclic alcohol compound) in the asymmetric reduction reaction of the present invention can be conducted according to the conventionally used methods. For example, in the case of the asymmetric reduction with CBS catalyst, an objective optically active alcohol compound can be obtained by optionally adding water, hydrochloric acid and the like to reaction solution to inactivate the catalyst, and then, extracting/concentrating the reaction product with suitable solvent (ethyl acetate, toluene, etc.), and dissolving the resulting residue in a minimum amount of solvent such as chloroform followed by column chromatography or crystallization in a suitable solvent. Also in the case of the asymmetric reduction with asymmetric transition metal complex, an objective optically active alcohol compound can be obtained, for example, according to the similar manner.

As the optically active alcohol compound obtained by the present invention, there may be mentioned, for example, an optically active cyclic alcohol compound represented by the general formula [S-I]:

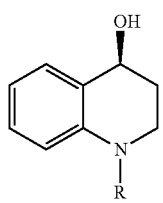

[S-I]

[wherein R represents a hydrogen atom or a protecting group for amino group.]

or the general formula [R-I]:

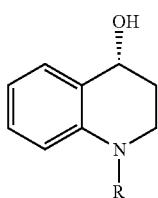

[R-I]

or salts thereof. R is preferably a hydrogen atom or a benzyloxycarbonyl group.

The separation/purification operations may be carried out after optionally introducing a suitable protecting group to a hydroxyl group at 4-position of the alcohol compound [I] in advance. The protecting group for the hydroxyl group at 4-position may include, for example, tert-butyldimethylsilyl group, a trifluoroacetyl group, a triethylsilyl group, a benzyloxycarbonyl group, a benzyl group, an acetyl group and the like. Among them, tert-butyldimethylsilyl group is preferred. It is also possible to subject the reaction product to separation/purification after removal of the protecting group at 1-position by conventional methods following the introduction of the protecting group to the hydroxyl group at 4-position. The protecting group at 1-position may include, for example, an aryl-lower alkylcarbonyl group such as benzyloxycarbonyl group, a lower alkoxycarbonyl group such as an ethoxycarbonyl group or a tert-butoxycarbonyl group, or a lower alkanoyl group optionally substituted by a halogen(s) such as an acetyl group or a trifluoroacetyl group, etc. Among them, a benzyloxycarbonyl group is preferred.

By using the optically active cyclic alcohol compound [I] obtained as mentioned above, the optically active naphthalene compound [A] can be prepared, for example, according to the following manners.

Namely, the compound [A] can be prepared according to the following steps:

(i) introducing a protecting group to a hydroxyl group at 4-position of the optically active cyclic alcohol compound [I] to prepare a compound represented by general formula [Ia]:

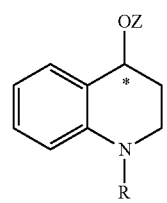

[Ia]

[wherein Z represents a protecting group for hydroxyl group, and other symbols have the same meaning as defined above.];

(ii) when the substituent (R) at 1-position of the compound [Ia] is a protecting group for amino group, removing the protecting group to prepare an optically active tetrahydroquinoline compound represented by general formula [Ib]:

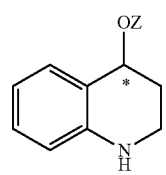

[Ib]

[wherein the symbols have the same meaning as defined above.];

(iii) reacting the compound [Ib] with a compound represented by general formula [III]:

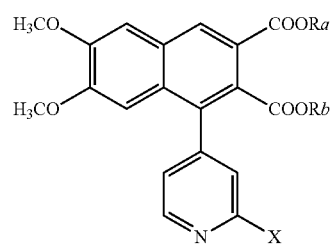

[III]

[wherein Ra and Rb are the same or different and each represents a hydrogen atom or a protecting group for carboxyl group, and X represents a halogen atom.]

to prepare an optically active naphthalene compound represented by general formula [IV]:

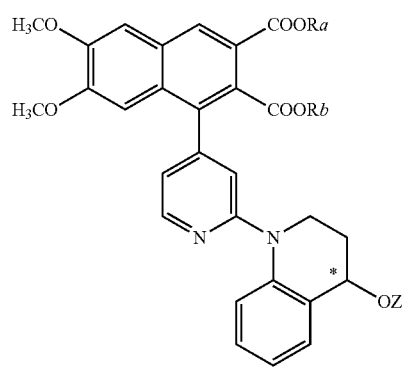

[IV]

[wherein the symbols have the same meaning as defined above.];

(iv) reducing the compound [IV] to prepare an optically active 2,3-bishydroxymethylnaphthalene compound represented by general formula [V]:

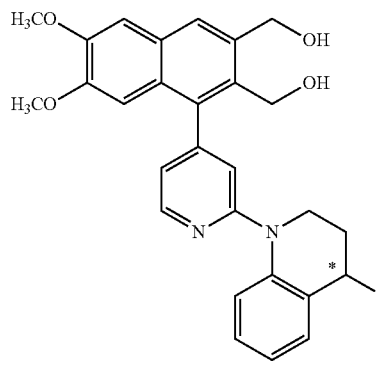

[wherein the symbols have the same meaning as defined above.]; and (v) removing the protecting group Z for hydroxyl group from the compound [V].

The protecting group for carboxyl group may include, for example, a lower alkyl group and the like.

Step (i): The introduction of the protecting group (Z) to a hydroxyl group at 4-position of the optically active cyclic alcohol compound [I] can be carried out according to the conventional manners. For example, the compound [Ia] having tert-butyldimethylsilyl group as the protecting group can be prepared by reacting the compound [I] having a hydroxyl group at 4-position with tert-butyldimethylsilyl halide (for example, tert-butyldimethylsilyl chloride) in a suitable solvent (N,N-dimethylformamide, etc.) in the presence of base (imidazole, etc.), at 0° C. to 50° C., for 30 minutes to 3 hours.

Step (ii): When 1-position of the compound [Ia] is a protecting group for amino group, removal of the protecting group can be carried out according to conventional manners. For example, removal of the protecting group from the compound [Ia] having a benzyloxycarbonyl group as the protecting group can be carried out by subjecting the compound to catalytic hydrogenation reaction under the condition: in the presence of catalyst (palladium carbon, etc.), in a suitable solvent (ethanol, etc.), under hydrogen atmosphere (1 atm to 3 atm), at 0° C. to 50° C., for 30 minutes to 3 hours.

Also, removal of the protecting group from the compound [Ia] having a tert-butoxycarbonyl group as the protecting group can be carried out by reacting said compound with an acid (hydrochloric acid, etc.) in a suitable solvent (ether, etc.) at 0° C. to 50° C. for 30 minutes to 3 hours. Removal of the protecting group from the compound [IV] having an acetyl group or a trifluoroacetyl group as the protecting group can be carried out by hydrolyzing said compound with base (sodium hydroxide, etc.) in a suitable solvent (hydrous ethanol, etc.) at 0° C. to 50° C. for 30 minutes to 3 hours.

Step (iii): Reaction between the compound [Ib] and the compound [III] can be carried out, for example, in solvent in the presence of palladium catalyst, base and phosphine ligand. The compound [Ib] may include, for example, a compound of the following general formula [S-Ib]:

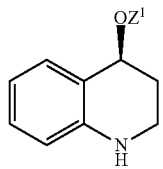

[wherein $Z^1$ represents tert-butyldimethylsilyl group.]
or a compound of the following general formula [R-Ib]:

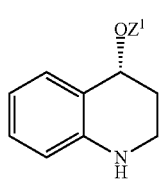

[wherein $Z^1$ represents tert-butyldimethylsilyl group.].

Any solvent may be used so long as it has no influence on the present reaction. Such a solvent may include, for example, toluene, xylene, N,N-dimethylformamide, 1,4-dioxane, dimethylsulfoxide, 1-butanol, acetonitrile, or combination thereof, etc. Palladium catalyst may include, for example, palladium acetate, palladium chloride, bis(acetylacetonato)palladium, tris(dibenzylideneacetone)dipalladium, 1,1'-bis(diphenylphosphino)ferrocene palladium dichloride and the like. The base may include, for example, alkali metal lower alkoxide such as sodium tert-butoxide, inorganic base such as cesium carbonate and potassium carbonate, and the like. The phosphine ligand may include, for example, tri-(tert-butyl)phosphonium-tetrafluoroborate, di-(tert-butyl)phosphonium-tetrafluoroborate, tri-(n-butyl)phosphonium-tetrafluoroborate, tri-(tert-butyl)phosphine and the like.

An amount of the compound [Ib] to be used is 1.0 to 2.0 equivalent(s), preferably 1.1 to 1.5 equivalents to the compound [III]. An amount of the palladium catalyst to be used is 0.01 to 1 equivalent, preferably 0.02 to 0.2 equivalent to the compound [Ib] or the compound [III]. An amount of the base to be used is 0.5 to 5 equivalent(s), preferably 1 to 2 equivalent(s) to the compound [Ib] or the compound [III]. An amount of the phosphine ligand to be used is 0.01 to 0.5 equivalent, preferably 0.02 to 0.1 equivalent to the compound [Ib] or the compound [III].

Reaction temperature of the present reaction is 25 to 150° C., preferably 80 to 120° C. Reaction time, which may differ depending on reaction conditions, is usually 10 minutes to 8 hours, preferably 30 minutes to 6 hours.

Step (iv): Reduction of the compound [IV] can be carried out in a solvent in the presence of a reducing agent. Any solvent can be used so long as it has no influence on the present reaction. Such a solvent may include, for example, methanol, tetrahydrofuran, ethanol, N,N-dimethylformamide, dimethylsulfoxide, 1,2-dimethoxyethane, or combination thereof, etc. The reducing agent may include, for example, metal hydride such as sodium borohydride, sodium bis(2-methoxyethoxy)aluminum hydride, and lithium aluminium hydride, etc. An amount of the reducing agent to be used is 1 to 30 equivalent(s), preferably 5 to 20 equivalents to the compound [IV].

Reaction temperature of the present reaction is 0 to 60° C., preferably 15 to 40° C. Reaction time, which may differ depending on reaction conditions, is usually 10 minutes to 8 hours, preferably 30 minutes to 5 hours.

Step (v): Removal of the protecting group Z from the compound [V] can be carried out, like the removal reaction of the protecting group for amino group in the above step (ii), depending on the variety of the protecting group, by conventional manners such as hydrolysis (when the protecting group is an acetyl group), acid treatment (when the protecting group is triethylsilyl group or tert-butoxycarbonyl group) and reduction (when the protecting group is a benzyloxycarbonyl group or a benzyl group). Also, when the protecting group is tert-butyldimethylsilyl group, the protecting group can be easily removed, for example, by the reaction in acetic acid in the presence of tetrabutylammonium fluoride.

According to the present invention, an optically active naphthalene compound represented by general formula [A]:

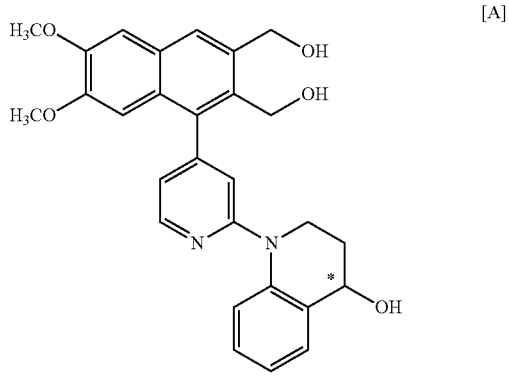

[A]

[wherein * represents an asymmetric carbon atom.]
and hydrates thereof or pharmaceutically acceptable salts thereof can be obtained.

One of such an optically active naphthalene compound is 1-[2-[(4S)-4-hydroxy-1,2,3,4-tetrahydroquinolin-1-yl]-4-pyridyl]-2,3-bis(hydroxymethyl)-6,7-dimethoxynaphthalene, and hydrates thereof or pharmaceutically acceptable salts thereof.

One of such an optically active naphthalene compound is 1-[2-[(4R)-4-hydroxy-1,2,3,4-tetrahydroquinolin-1-yl]-4-pyridyl]-2,3-bis(hydroxymethyl)-6,7-dimethoxynaphthalene, and hydrates thereof or pharmaceutically acceptable salts thereof.

Incidentally, the raw material compound [II] in the present invention can be prepared, for example, according to the method described in Journal of Medicinal Chemistry, Vol. 8, pp. 566-571 (1965). Also, the raw material compound [III] can be prepared, for example, according to the method described in European Patent No. 748805.

In the present specification, "a lower alkyl" represents an alkyl having 1 to 6 carbon atom(s), "a lower alkoxy" represents an alkoxy having 1 to 6 carbon atom(s), "a lower alkanoyl" represents an alkanoyl having 2 to 7 carbon atoms, "an aryl" represents 6 to 10 membered monocyclic or bicyclic aryl, "an aromatic heterocycle" represents 5 to 10 membered aromatic heterocycle containing 1 or more hetero atom(s) selected from sulfur atom, oxygen atom and nitrogen atom.

EXAMPLES

In the following, the present invention is explained in more detail by the following examples, but the examples do not limit the present invention.

Example 1

(1) 5.04 g of 4-oxo-1,2,3,4-tetrahydroquinoline was dissolved in 20 mL of tetrahydrofuran at 25° C. To the solution were added 5.6 mL of benzyloxycarbonyl chloride, 15 mL of water and 4.73 g of potassium carbonate under ice-cooling, and the mixture was stirred at 25° C. for 24 hours. To the reaction solution was added ethyl acetate, and the organic layer was separated, dried over magnesium sulfate, and then filtered. The filtrate was concentrated and the residue was dissolved in 35 mL of isopropyl alcohol under heating. The solution was cooled gradually, and the precipitated crystals were collected by filtration under ice-cooled condition. The resulting crystals were washed with 25 mL of cold isopropyl alcohol, and then dried at 50° C. for 16 hours to give 8.98 g of 1-benzyloxycarbonyl-4-oxo-1,2,3,4-tetrahydroquinoline (93% yield).

MS (APCI) m/z: 282 [M+H]$^+$
IR (ATR) v=1708, 1683 cm$^{-1}$
$^1$H-NMR (CDCl$_3$) δ: 8.00 (dd, J=7.8, 1.6 Hz, 1H), 7.82 (d, J=8.4 Hz, 1H), 7.51 (dt, J=1.6, 7.8 Hz, 1H), 7.43-7.34 (m, 5H), 7.19 (t, J=7.5 Hz, 1H), 5.29 (s, 2H), 4.25-4.22 (m, 2H), 2.80-2.77 (m, 2H)

(2) To a mixture of 1.0 mL of (R)-2-methyl-CBS-oxazaborolidine solution and 5 mL of tetrahydrofuran was added dropwise 1.4 mL of 1.0M borane-tetrahydrofuran complex at 25° C., and the mixture was stirred at the same temperature for 15 minutes. To the reaction solution was added dropwise a solution of 281 mg of the compound obtained in the above (1) in 7 mL of tetrahydrofuran over 5 minutes. To the reaction solution was added dropwise 1 mL of methanol, and then the reaction solution was concentrated under reduced pressure. To the residue were added 10 mL of dichloromethane and 10 mL of phthalate buffer (pH4.0). The aqueous layer was removed from the mixture and then to the mixture was added water. The organic layer was separated and dried over magnesium sulfate, and then filtered. The filtrate was concentrated and the resulting residue was purified by column chromatography on silica gel (solvent; hexan/ethyl acetate=2/1) to give 283 mg of (4S)-1-benzyloxycarbonyl-4-hydroxy-1,2,3,4-tetrahydroquinoline (yield: quantitative, optical purity: 97% ee).

MS (APCI) m/z: 301 [M+H]$^+$
IR (ATR) v=3417, 1686 cm$^{-1}$
$^1$H-NMR (CDCl$_3$) δ: 7.87 (d, J=8.2 Hz, 1H), 7.42-7.23 (m, 7H), 7.10 (dt, J=1.3, 7.4 Hz, 1H), 5.27 (d, J=12 Hz, 1H), 5.22 (d, J=12 Hz, 1H), 4.79 (dd, J=9.5, 4.6 Hz, 1H), 4.17-4.10 (m, 1H), 3.73-3.65 (m, 1H), 2.14-1.99 (m, 2H), 1.79 (d, J=4.9 Hz, 1H)

Also, the optical purity (enantiomeric excess: ee) of the objective substance was measured under the following condition (in Example herebelow, unless otherwise indicated, the optical purity was measured in the same manner as this).
Column used: CHIRALPAK AD-H (DAICEL CHEMICAL INDUSTRIES, LTD.)
Mobile phase: ethanol/n-hexan=20/80

(3) To a solution of 28.33 g of the compound obtained in the above (2) in 424 mL of N,N-dimethylformamide were added 40.85 g of imidazole and 45.22 g of tert-butyldimethylsilyl chloride at room temperature, and the mixture was stirred at the same temperature for 1 hour. The reaction solution was concentrated, and then to the residue were added 280 mL of ethyl acetate and 140 mL of water, which was washed. The organic layer was washed with 140 mL of 10% aqueous citric acid solution, 140 mL of 3% aqueous sodium hydrogen carbonate solution and 57 mL of 20% saline, dried over magnesium sulfate, and then dried. The filtrate was concentrated under reduced pressure to give 39.28 g of (4S)-1-benzyloxycarbonyl-4-tert-butyldimethylsilyloxy-1,2,3,4-tetrahydroquinoline (yield: 98.8%).

(4) To a solution of 39.28 g of the compound obtained in the above (3) in 393 mL of ethanol was added 1.96 g of palladium carbon in a nitrogen atmosphere, and then the mixture was stirred under hydrogen atmosphere for 4 hours. The reaction solution was filtered and the filtrate was concentrated. The resulting residue was purified by column chromatography on silica gel (solvent; n-hexan/ethyl acetate=30/1 to 20/1) to give 14.82 g of (4S)-4-tert-butyldimethylsilyloxy-1,2,3,4-tetrahydroquinoline (yield: 56.9%, optical purity: 98.8% ee).

$[\alpha]_D^{28} = -128.6°$ (methanol, c=1.10)

$^1$H-NMR (CDCl$_3$) δ: 7.13 (d, J=7.7 Hz, 1H), 7.04 (t, J=6.9 Hz, 1H), 6.63 (t, J=7.4 Hz, 1H), 6.48 (d, J=7.7 Hz, 1H), 4.78 (t, J=4.4 Hz, 1H), 3.7-3.9 (br, 1H), 3.41-3.45 (m, 1H), 3.24-3.28 (m, 1H), 1.18-1.94 (m, 2H), 0.91 (s, 9H), 0.15 (s, 3H), 0.10 (s, 3H)

Also, the optical purity (enantiomeric excess: ee) of the objective substance was measured under the following condition.
Column used: CHIRALCEL OJ-H (DAICEL CHEMICAL INDUSTRIES, LTD.)
Mobile phase: methanol/n-hexan=1/99

Example 2

To a mixture of 0.5 mL of (R)-2-methyl-CBS-oxazaborolidine solution and 3 mL of dichloromethane was added dropwise 0.07 mL of 1.0M borane-dimethylsulfide complex at 25° C., and the mixture was stirred at the same temperature for 15 minutes. To the solution was added dropwise a solution of 141 mg of 1-benzyloxycarbonyl-4-oxo-1,2,3,4-tetrahydroquinoline in 2.5 mL of dichloromethane over about 10 minutes. Furthermore, to the reaction solution were added 0.07 mL of 1.0M borane-dimethylsulfide complex and a solution of 141 mg of 1-benzyloxycarbonyl-4-oxo-1,2,3,4-tetrahydroquinoline in 2.5 mL of dichloromethane alternately with total 4 times. To the reaction solution was added dropwise 1 mL of methanol, and the reaction solution was concentrated. To the resulting residue were added 10 mL of dichloromethane and 10 mL of phthalate buffer (pH4.0), and the aqueous layer was removed, and then water was added. The organic layer was separated, dried over magnesium sulfate, and then filtered, and the filtrate was concentrated. The resulting residue was purified by column chromatography on silica gel (solvent; n-hexan/ethyl acetate=4/1) to give 559 mg of (4S)-1-benzyloxycarbonyl-4-hydroxy-1,2,3,4-tetrahydroquinoline (yield: 99%, optical purity: 96% ee).

MS (APCI) m/z: 301 [M+NH$_4$]$^+$

Example 3

147 mg of 4-oxo-1,2,3,4-tetrahydroquinoline was treated in the same manner as Example 1 (2) to give 135 mg of (4S)-4-hydroxy-1,2,3,4-tetrahydroquinoline (yield: 90%, optical purity: 96% ee).

MS (ESI) m/z: 150 [M+H]$^+$
IR (ATR) ν=3231 cm$^{-1}$
1H-NMR (CDCl$_3$) δ: 7.21 (dd, J=7.4, 1.5 Hz, 1H), 7.10-7.05 (m, 1H), 6.67 (dt, J=1.0, 7.4 Hz, 1H), 6.53 (dd, J=7.9, 1.0 Hz, 1H), 4.78-4.73 (m, 1H), 3.41 (dt, J=3.1, 12 Hz, 1H), 3.29-3.23 (m, 1H), 2.06-1.99 (m, 1H), 1.96-1.75 (m, 2H)

Also, the optical purity (enantiomeric excess: ee) of the objective substance was measured under the following condition.
Column used: CHIRALCEL OJ-H (DAICEL CHEMICAL INDUSTRIES, LTD.)
Mobile phase: ethanol/n-hexan=10/90

Example 4

A mixture of 30.6 mg of [RuI$_2$(p-cymene)]$_2$, 73.3 mg of (S,S)-TsDPEN and 25 mL of isopropyl alcohol was heated in a nitrogen stream at 80° C. for 1 hour. The reaction solution was cooled to 25° C., and then to the reaction solution were added 281 mg of 1-benzyloxycarbonyl-4-oxo-1,2,3,4-tetrahydroquinoline, 28.1 mg of potassium hydroxide and 10 mL of isopropyl alcohol in series. The mixture was stirred at 25° C. for 23 hours. To the reaction solution was added 10 mL of 0.1N hydrochloric acid and the mixture was stirred, and then concentrated under reduced pressure, and to the residue was added 10 mL of ethyl acetate. The organic layer was separated, dried over magnesium sulfate, and then filtered. The filtrate was concentrated, and the resulting residue was purified by column chromatography on silica gel (solvent; hexan/ethyl acetate=4/1) to give 270 mg of (4S)-1-benzyloxycarbonyl-4-hydroxy-1,2,3,4-tetrahydroquinoline (optical purity: 99% ee, yield: 95%).

Example 5

1-benzyloxycarbonyl-4-oxo-1,2,3,4-tetrahydroquinoline (281 mg), [RuCl$_2$(benzene)]$_2$ (25.0 mg) and (S,S)-TsDPEN (73.3 mg) were treated in the same manner as Example 4 to give 244 mg of (4S)-1-benzyloxycarbonyl-4-hydroxy-1,2,3,4-tetrahydroquinoline (optical purity: 97% ee, yield: 86%).

Example 6

(1) A solution of 20.00 g of 1-(2-bromo-4-pyridyl)-2,3-bis(methoxycarbonyl)-6,7-dimethoxynaphthalene in 200 mL of toluene was sonicated under reduced pressure, and then to the solution were added 975 mg of palladium acetate, 1009 mg of tri-tert-butylphosphonium tetrafluoroborate, 13.72 g of (4S)-4-(tert-butyldimethylsilyloxy)-1,2,3,4-tetrahydroquinoline and 6.26 g of sodium tert-butoxide at room temperature. After nitrogen substitution, the mixture was stirred at 100° C. for 4 hours. After radiation, to the reaction solution were added 100 mL of saturated aqueous ammonium chloride solution, 100 mL of water and 100 mL of ethyl acetate, and the mixture was filtered through Celite®. Celite® was washed with 100 mL of ethyl acetate, and then the organic layer was separated. The organic layer was washed with 100 g of 20% saline, dried over magnesium sulfate, and then concentrated. The resulting residue was purified by column chromatography on silica gel (n-hexan/ethyl acetate=5/1 to 4/1) to give 22.31 g of 1-[2-[(4S)-4-(tert-butyldimethylsilyloxy)-1,2,3,4-tetrahydroquinolin-1-yl]-4-pyridyl]-2,3-bis(methoxycarbonyl)-6,7-dimethoxynaphthalene (yield: 80%).

MS (APCI) m/z: 643 [M+H]$^+$
$[\alpha]_D^{28} = -62°$ (methanol, c=1)

(2) To a solution of 21.21 g of the compound obtained in the above (1) in 212 mL of tetrahydrofuran was added 8.74 g of sodium borohydride at room temperature, and then to the solution was added dropwise 16.9 mL of methanol at 60° C. over 2 hours. Furthermore, to the reaction solution was added 8.74 g of sodium borohydride at the same temperature, and to it was added dropwise 16.9 mL of methanol over 2 hours. After radiation, to the reaction solution was added 212 g of 20% saline, which was extracted with 212 mL of ethyl acetate. The aqueous layer was extracted with 212 mL of ethyl acetate, and the combined organic layers were washed with 212 g of 20% saline, dried over 10.6 g of magnesium sulfate, and then concentrated under reduced pressure. The resulting residue was purified by column chromatography on silica gel (solvent; n-hexan/ethyl acetate=1/1 to 2/1) to give 17.86 g of 1-[2-[(4S)-4-(tert-butyldimethylsilyloxy)-1,2,3,4-tetrahydroquinolin-1-yl]-4-pyridyl]-2,3-bis(hydroxymethyl)-6,7-dimethoxynaphthalene (yield: 92%).

MS (APCI) m/z: 587 [M+H]$^+$
$[\alpha]_D^{28} = -77°$ (methanol, c=1)

(3) To 17.00 g of the compound obtained in the above (2) were added 8.3 mL of acetic acid and 289 mL of 1M tetrabutylammonium fluoride-tetrahydrofuran solution in water bath, and the mixture was stirred at room temperature for 4 hours. To the reaction solution was added further 145 mL of 1M tetrabutylammonium fluoride-tetrahydrofuran solution at room temperature, and the mixture was stirred at the same temperature for 2 hours. To the reaction solution were added 6% aqueous sodium hydrogen carbonate solution and 25% saline, which was extracted with ethyl acetate. The extracts were dried over magnesium sulfate and then filtered, and the filtrate was concentrated under reduced pressure. The resulting residue was purified by column chromatography on silica gel (solvent; chloroform/methanol=99/1 to 96/4) to give 10.4 g of 1-[2-[(4S)-4-hydroxy-1,2,3,4-tetrahydroquinolin-1-yl]-4-pyridyl]-2,3-bis(hydroxymethyl)-6,7-dimethoxynaphthalene (yield: 72%) as a crude product. To a solution of 10.2 g of the compound in 30.6 mL of ethanol was added 10.6 mL of water at 40° C. After precipitating crystals, 306 mL of water was further added and the mixture was cooled. The precipitated crystals were collected by filtration and washed with 20.6 mL of water, and then dried under reduced pressure at room temperature to give 8.66 g of 1-[2-[(4S)-4-hydroxy-1,2,3,4-tetrahydroquinolin-1-yl]-4-pyridyl]-2,3-bis(hydroxymethyl)-6,7-dimethoxynaphthalene sesquihydrate (yield: 85%, optical purity: 99.9% ee) as crystals.

MS (APCI) m/z: 493 [M+H]$^+$
$[\alpha]_D^{22} = -92.2°$ (methanol, c=1)
Water content: 5.35% (Karl Fischer's method)
$^1$H-NMR (CDCl$_3$) δ: 8.46 (t, J=5.3 Hz, 1H), 7.71 (d, J=6.6 Hz, 1H), 7.37-7.39 (m, 2H), 7.18 (s, 1H), 7.13 (d, J=8.2 Hz, 1H), 7.05-7.10 (m, 1H), 6.85-6.95 (m, 1H), 6.80-6.85 (m, 1H), 6.71 (d, J=14.8 Hz, 1H), 4.79-4.93 (m, 3H), 4.58-4.70 (m, 2H), 4.22-4.25 (m, 1H), 4.00 (d, J=6.9 Hz, 3H), 3.88-3.99 (m, 1H), 3.78 (d, J=17.9 Hz, 3H), 3.03-3.11 (br, 2H), 2.03-2.16 (m, 3H)

Also, the optical purity (enantiomeric excess: ee) of the objective substance was measured under the following condition.
Column used: SUMICHIRAL OA-4900 (Sumika Chemical Analysis Service, Ltd.)
Mobile phase: n-hexan/ethanol/tetrahydrofuran/trifluoroacetic acid=350/100/50/1

REFERENCE EXAMPLE (1) To a solution of 500 g of 3,4-dimethoxybenzaldehyde in 2.5 L of methanol was added dropwise 529 g of bromine at room temperature (under cooling, if necessary) over 1 hour, and the mixture was stirred at the same temperature for 3 hours. To the reaction solution was added dropwise 2.5 L of water, and the crystals were precipitated. To the crystal suspension was added 20% aqueous sodium hydroxide solution at room temperature to adjust it to pH about 9 to 10, and then cooled. The precipitated crystals were collected by filtration and washed with water, and then dried at 50° C. for 12 hours to give 718.78 g of 6-bromo-3,4-dimethoxybenzaldehyde (yield: 98%).

(2) To a suspension of 612.68 g of the compound obtained in the above (1), 397.88 g of trimethyl orthoformate and 612 mL of methanol was added 4.76 g of p-toluenesulfonic acid, and the mixture was refluxed under heating for 3 hours. After radiation, to the mixture was added 2.70 g of 28% sodium methylate-methanol solution, which was concentrated. The residue was dissolved in 1.2 L of toluene, and then concentrated, and the residue was dissolved in 1.2 L of toluene again and then concentrated to give 762.85 g of 6-bromo-3,4-dimethoxybenzaldehyde dimethylacetal (yield: quantitative).

(3) To a solution of 2.91 g of the compound obtained in the above (2) in 9 mL of tetrahydrofuran was added dropwise 6.25 mL of 1.6M n-butyl lithium-hexan solution in a nitrogen atmosphere under cooling with dry ice-acetone, and the mixture was stirred at the same temperature for 30 minutes. To the reaction solution was added dropwise a solution of 1.86 g of 2-bromo-4-formylpyridine in 9 mL of tetrahydrofuran, and the mixture was stirred for 1 hour. To the reaction solution was added 30 mL of saturated aqueous ammonium chloride solution, which was extracted with 30 mL of ethyl acetate. The aqueous layer was extracted with 30 mL of ethyl acetate again, and the extracts were combined and washed with saturated saline, then dried over magnesium sulfate, and concentrated under reduced pressure. The residue was triturated with 100 mL of chloroform, and concentrated under reduced pressure. The residue was purified by column chromatography on silica gel (solvent; n-hexan/ethyl acetate=3/1 to 1/1) to give 2.53 g of 3,4-dimethoxy-6-(2-bromo-4-pyridyl) (hydroxy) methylbenzaldehyde dimethylacetal (yield: 64%).

(4) A mixture of 4.00 g of the compound obtained in the above (3), 1.59 g of dimethyl fumarate, 20 mL of xylene and 2 g of acetic acid was refluxed under heating for 2 hours. After radiation, the solution was concentrated under reduced pressure, and to the residue was added 8 mL of toluene, which was concentrated. To the resulting residue was added 8 mL of acetonitrile, and then added dropwise 3.55 g of boron trifluoride-diethylether in an ice-water bath. The mixture was refluxed under heating for 2 hours. After radiation, the reaction solution was concentrated under reduced pressure. To the residue was added 28 mL of chloroform, which was ice-cooled. To the mixture was added dropwise 3.41 g of 25% aqueous ammonia at 25° C. or below, and then the mixture was stirred at 45 to 50° C. for 15 minutes. To the reaction solution was added 24 mL of water, and then the organic layer was washed with 20 mL of water and 28 g of 20% saline, dried over magnesium sulfate, and then concentrated under reduced pressure. To the resulting residue was added 12 mL of methanol and the mixture was heated. The solution was cooled, and the precipitated crystals were collected by filtration to give 3.67 g of 1-(2-bromo-4-pyridyl)-2,3-bis(methoxycarbonyl)-6,7-dimethoxynaphthalene (yield: 79.7%) as crystals.

UTILIZABILITY IN INDUSTRY

According to the present invention, an optically active cyclic alcohol compound useful as a synthetic intermediate for pharmaceutical compounds such as an optically active naphthalene compound (PDE4 inhibitor) can be prepared with industrial advantage.

The invention claimed is:

1. A method for preparing a non-racemic naphthalene compound represented by general formula [A]:

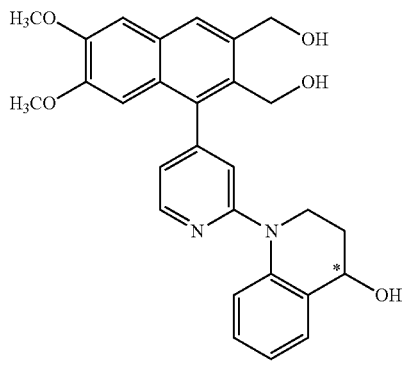

which comprises the following steps of (a) to (c):

(a) reacting a compound represented by general formula [Ib]:

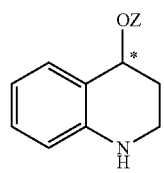

wherein Z represents a protecting group for hydroxyl group, and * represents an asymmetric carbon atom, with a compound represented by general formula [III]:

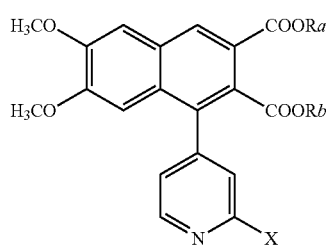

wherein Ra and Rb are the same or different and each represents a hydrogen atom or a protecting group for carboxyl group, and X represents a halogen atom, to obtain a non-racemic naphthalene compound represented by general formula [IV]:

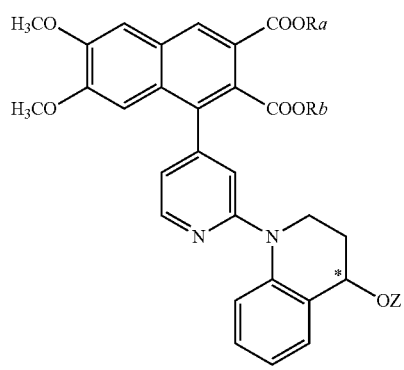

wherein the symbols have the same meaning as defined above;

(b) reducing the compound [IV] to obtain an optically active 2,3-bishydroxymethylnaphthalene compound represented by general formula [V]:

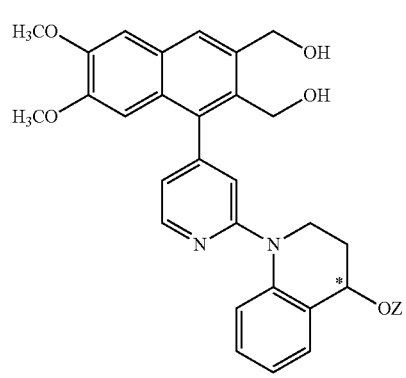

wherein the symbols have the same meaning as defined above; and (c) removing the protecting group Z for hydroxyl group from the compound [V].

2. The method according to claim 1, wherein the compound [Ib] is a compound of the following general formula [S-Ib]:

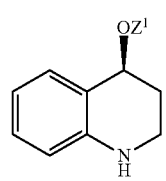

wherein $Z^1$ represents a tert-butyldimethylsilyl group.

3. The method according to claim 1, wherein the compound [Ib] is a compound of the following general formula [R-Ib]:
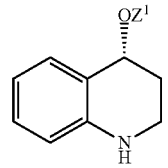
[R-Ib]
wherein $Z^1$ represents a tert-butyldimethylsilyl group.
* * * * *